(12) United States Patent
Thoret Bauchet

(10) Patent No.: US 8,722,954 B2
(45) Date of Patent: May 13, 2014

(54) USE OF SOLVENT TO DECREASE CAUSTIC SCRUBBER FOULING

(75) Inventor: Jean-Pierre Thoret Bauchet, Brussels (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 0 days.

(21) Appl. No.: 13/695,076

(22) PCT Filed: May 3, 2011

(86) PCT No.: PCT/EP2011/057007
§ 371 (c)(1),
(2), (4) Date: Jan. 2, 2013

(87) PCT Pub. No.: WO2011/138305
PCT Pub. Date: Nov. 10, 2011

(65) Prior Publication Data
US 2013/0237740 A1    Sep. 12, 2013

(30) Foreign Application Priority Data
May 7, 2010 (EP) .................................... 10162290

(51) Int. Cl.
*C10G 75/04* (2006.01)
(52) U.S. Cl.
USPC .................... 585/809; 208/48 AA; 208/48 R; 208/283; 585/950
(58) Field of Classification Search
None
See application file for complete search history.

(56) References Cited

U.S. PATENT DOCUMENTS

| 3,696,162 A | 10/1972 | Kniel |
| 4,041,129 A * | 8/1977 | Foster et al. ................. 423/234 |
| 4,343,777 A | 8/1982 | Dannhor et al. |
| 4,673,489 A | 6/1987 | Roling |

(Continued)

FOREIGN PATENT DOCUMENTS

| EP | 0264280 A2 | 10/1986 |
| JP | 49027844 A1 | 7/1974 |

(Continued)

OTHER PUBLICATIONS

Office Action issued in Japanese Patent Application No. 2013-509503, dated Jan. 7, 2014 (4 pages).

*Primary Examiner* — Tam M Nguyen

(57) ABSTRACT

The present invention is a method of reducing the formation of fouling deposits occurring in a caustic scrubber used to remove acid gases comprising: a) providing a caustic scrubber fed with an alkaline aqueous solution comprising essentially one or more of NaOH, KOH or LiOH, b) providing an olefin-containing hydrocarbon stream, contaminated with oxygenated compounds and acid gases, and said oxygenated compounds are capable to make polymeric fouling deposits in the presence of the alkaline solution of the scrubber, c) sending the above hydrocarbon stream to the caustic scrubber to recover an olefin-containing hydrocarbon stream essentially free of acid gases, wherein, d) an efficient amount of a solvent capable to reduce the formation of fouling deposits is introduced in the caustic scrubber and/or in the alkaline solution fed to the scrubber, e) the liquid outlet of the scrubber is sent to means to separate the solvent from the alkaline solution, and wherein the caustic scrubber has several stages with various caustic concentrations, and wherein the solvent injection and removal can be located at each stage.

13 Claims, 6 Drawing Sheets

(56) References Cited

U.S. PATENT DOCUMENTS

| | | | |
|---|---|---|---|
| 4,952,301 A | 8/1990 | Awbrey | |
| 5,194,143 A * | 3/1993 | Roling | 208/291 |
| 5,220,104 A | 6/1993 | McDaniel et al. | |
| 5,582,808 A * | 12/1996 | Patek | 423/210 |
| 5,714,055 A | 2/1998 | Lewis et al. | |
| 5,770,041 A * | 6/1998 | Lewis et al. | 208/48 AA |
| 5,885,422 A * | 3/1999 | Kurukchi et al. | 203/45 |
| 6,210,583 B1 | 4/2001 | Kurukchi et al. | |
| 6,372,121 B1 | 4/2002 | McClain et al. | |
| 2003/0116018 A1 | 6/2003 | Echizen et al. | |
| 2003/0205503 A1 * | 11/2003 | Subramaniyam et al. | 208/48 AA |

FOREIGN PATENT DOCUMENTS

| | | |
|---|---|---|
| JP | 08269470 | 10/1996 |
| JP | 2001305287 | 10/2001 |
| JP | 2004275831 | 10/2004 |
| WO | 0164609 A1 | 9/2001 |
| WO | 0236715 A1 | 5/2002 |
| WO | 03104170 A1 | 12/2003 |
| WO | 2004003110 A1 | 1/2004 |

* cited by examiner

Conditions: 40°C, 1% precursor, 30 minutes, 8% Caustic.

Conditions: 40°C, 30 minutes, 8% Caustic.

Conditions: 40°C, 30 minutes, 8% Caustic.

Conditions: 40°C, 1% acetaldehyde.

Conditions: 8% caustic, 1% acetaldehyde.

Conditions: 15 minutes, 1% Acetaldehyde.

Conditions: 1% Acetaldehyde.

Conditions: 1% Acetaldehyde.

USE OF SOLVENT TO DECREASE CAUSTIC SCRUBBER FOULING

CROSS-REFERENCE TO RELATED APPLICATIONS

This application claims the benefit of PCT/EP2011/057007, filed May 3, 2011, which claims priority from EP 10162290.0, filed May 7, 2010.

FIELD OF THE INVENTION

The present invention relates to the use of solvent to decrease caustic scrubber fouling. Olefins are traditionally produced from petroleum feedstocks by catalytic or steam cracking processes. These cracking processes, especially steam cracking, produce light olefin(s), such as ethylene and/or propylene, from a variety of hydrocarbon feedstock. The limited supply and increasing cost of crude oil has prompted the search for alternative processes for producing hydrocarbon products. The MTO process produces light olefins such as ethylene and propylene as well as heavy hydrocarbons such as butenes. Said MTO process is the conversion of methanol or dimethylether by contact with a molecular sieve. The interest in the methanol to olefin (MTO) process is based on the fact that methanol can be obtained from coal or natural gas by the production of synthesis gas which is then processed to produce methanol. Olefins can also be produced by dehydration of alcohols. Ethanol can be obtained by fermentation of carbohydrates. Made up of organic matter from living organisms, biomass is the world's leading renewable energy source.

The olefins recovered from an MTO process or an alcohol dehydration process comprise oxygenated contaminants as well as acid gases such as CO2. In the course of the olefins purification acid gases are removed in equipment referred to as "caustic scrubbers" or "caustic towers". The present invention refers to the fouling of said caustic scrubbers.

BACKGROUND OF THE INVENTION

Pyrolysis is the transformation of a compound into one or more other substances by heat alone. In the petroleum and petrochemical industries, pyrolysis is useful for the processing of hydrocarbons. This process is often referred to as "cracking". When the pyrolysis of hydrocarbons is conducted in the presence of steam, it is often referred to as "steam cracking". The steam cracking of ethane, propane, naphthas, gas oils and other hydrocarbon feedstocks is a useful process for producing valuable olefins. As a byproduct of the steam cracking process, oxygenated compounds, including carbonyl compounds, are formed. These carbonyl compounds include, but are not limited to, aldehydes and ketones. The amount of carbonyl compounds formed in cracking operations can vary widely, but is typically from about 1 ppm to about 200 ppm in the gas stream with concentrations as high as about 1000 ppm occasionally being encountered because of the use of various feedstocks and cracking temperatures. Byproducts of hydrocarbon cracking processes include the undesirable acid gases $CO_2$ and $H_2S$. Therefore, it is normal for a hydrocarbon cracking plant to have an acid gas removal system to remove $CO_2$ and $H_2S$ from the cracked gas. Typically the acid gas removal system usually consists of passing the gas steam through a basic wash (pH greater than 7) to remove acidic components, including hydrogen sulfide and carbon dioxide gas. In the petroleum and petrochemical industries, unit operations involving basic washes are commonly carried out in equipment referred to as 'caustic scrubbers' or 'caustic towers'.

In an acid gas removal system, some oxygenated compounds are also removed. It is known in the art of hydrocarbon processing that certain of these oxygenated compounds, especially carbonyl compounds and particularly acetaldehyde, will undergo polymerization in the presence of the base. When removing carbon dioxide with caustic, aldehydes are trapped. The aldehydes in the caustic solutions reacts producing polyaldols. These polymers known in the industry as Red Oils induce a fouling of the caustic scrubber. In the acid gas removal system, the acetaldehyde polymer will settle on internal equipment surfaces leading to fouling and eventual plugging. Fouling and plugging of the internal equipment means the unit must be shut down to perform cleaning. Every time a unit operation has to be shut down for cleaning it means that a cost is incurred due to lost production, over and above, the actual cost to clean the equipment.

Many prior arts are dealing with such fouling, they essentially describe the introduction of various chemical inhibitors in the caustic scrubber.

During the production of ethylene and propylene with oxygenated feedstock, such as an MTO and alcohol dehydration, aldehydes and carbon dioxide are produced. The amount of aldehydes produced in these processes is very high compared to the steam cracker. The other characteristic of these processes is that very low quantities of aromatics such as benzene are produced. As the concentration of aldehydes is very high, the fouling potential is also very important. In the caustic scrubber operating with the effluent of a steam cracker the presence of aromatics helps to reduce the red oils. On the contrary in the caustic scrubber operating with the effluent of an MTO or alcohol dehydration there are two drawbacks:
(i) there are more aldehydes, as a consequence the red oils are increased,
(ii) there are much less aromatics by produced, as a consequence the red oils are not dissolved and the fouling increased.

It has now been discovered to introduce a solvent, advantageously benzene or toluene or xylenes, in the caustic scrubber and/or in the alkaline solution fed to the scrubber to reduce the formation of the fouling deposits by reducing the Red Oils formation and not only by the dissolution of them.

Prior art has already described introduction of aromatics and/or solvents in a caustic scrubber in the proportion of an inhibitor, it has nothing to see with the proportions and function of the solvent of the present invention. This present solvent reduces the Red Oils formation rate by reducing the contact of growing polymers with Caustic.

U.S. Pat. No. 5,582,808 provides borohydrides that are useful in reducing aldol condensation and subsequent polymer formation in caustic scrubbers. The borohydrides are believed to react with reactive carbonyls yielding more stable alcohols and a salt of the borohydride which remains water soluble, and thus is unlikely to be carried out with the hydrocarbon phase. The borohydrides have the potential to reduce reactive carbonyls at a molar ratio as high as about 4:1:: carbonyl:borohydride. A preferred borohydride is sodium borohydride (sodium tetrahydroborate). The borohydride can be introduced in a solvent, toluene may be used but is not desirable (col 3 lines 6-10). Preferably the borohydride is introduced into a caustic solution.

U.S. Pat. No. 5,770,041 describes adding an effective deposit-inhibiting amount of a non-enolizable carbonyl compound to the caustic solution. Preferred non-enolizable carbonyl compounds are formaldehyde, glyoxal, benzaldehyde, p-anisaldehyde, formic acid, glyoxalic acid and paraformaldehyde. The non-enolizable carbonyl compound may be added to the spent caustic wash/stripper system in an amount representing a molar ratio of non-enolizable carbonyl to carbonyl from about 25:1 to about 3:1. Preferably, the ratio is from about 10:1 to about 3:1. Most preferably, the ratio is from about 5:1 to about 3:1. The solution should be added to the system in sufficient quantity to assure that the molar amount of inhibitor is effective to prevent fouling. Treatment ranges of from 1 to 10,000 ppm of inhibitor in the medium may be utilized if no convenient method of measuring carbonyl concentration is available. Where the carbonyl concentration is known or estimable, the inhibitor is preferably added in excess of the carbonyl equivalents. Solvents suitable to dilute the inhibitors include water, . . . pyrolysis gasoline. These two above prior arts don't mention the use of a solvent to reduce the fouling.

U.S. Pat. No. 5,714,055 describes adding an effective depositing-inhibiting amount of a caustic solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the caustic solution. A preferred substituted aromatic amine is the sodium salt of 4-aminobenzenesulfonic acid in aqueous solution. The substituted aromatic amine may be added to the alkaline scrubber in an amount representing a molar ratio of amine to carbonyl from about 1.0:10.0 to about 1.0:25.0. Preferably, the substituted aromatic amine may be added to the alkaline scrubber in an amount representing a molar ratio of amine to carbonyl from about 1.0:3.0 to about 1.0:9.0. Most preferably, the substituted aromatic amine may be added to the alkaline scrubber in an amount representing a molar ratio of amine to carbonyl from about 1.0:1.0 to about 1.0:2.0.

U.S. Pat. No. 5,194,143 discloses a method for inhibiting the formation of polymeric based fouling deposits normally formed during the caustic washing of hydrocarbons. The method comprises adding an effective amount for the purpose of an acetoacetate ester compound to the caustic wash system. One mole of the acetoacetate ester compound is needed for every one mole of aldehyde. The acetoacetate ester compound should be added to the caustic wash in an amount from about 0.5 to about 10 moles per mole of aldehyde. Preferably, the feed rate ranges to from 1 about 3 moles of acetoacetate ester compound per mole of aldehyde, with a 1.0 mole ratio being especially preferred. Broadly speaking, from about 1 to about 10,000 parts per million acetoacetate ester compound per million parts basic wash is a sufficient treatment range if no convenient method of measuring carbonyl level is available.

SUMMARY OF THE INVENTION

The present invention is a method of reducing the formation of fouling deposits occurring in a caustic scrubber used to remove acid gases comprising:
a) providing a caustic scrubber fed with an alkaline aqueous solution comprising essentially one or more of NaOH, KOH or LiOH,
b) providing an olefin-containing hydrocarbon stream, contaminated with oxygenated compounds and acid gases, and said oxygenated compounds are capable to make polymeric fouling deposits in the presence of the alkaline solution of the scrubber,
c) sending the above hydrocarbon stream to the caustic scrubber to recover an olefin-containing hydrocarbon stream essentially free of acid gases,
wherein,
d) an efficient amount of a solvent capable to reduce the formation of fouling deposits is introduced in the caustic scrubber and/or in the alkaline solution fed to the scrubber,
e) the liquid outlet of the scrubber is sent to means to separate the solvent from the alkaline solution,
f) optionally an additive capable to reduce the conversion of the oxygenated compounds to polymeric fouling deposits in the presence of the alkaline solution of the scrubber is introduced in the caustic scrubber and/or in the alkaline solution fed to the scrubber.

In an embodiment the solvent separated from the alkaline solution at step e) is treated to eliminate heavies and recycled at step d). Said treatment can be a stripping or a distillation.

In an embodiment the means of step e) to separate the solvent from the alkaline solution are located in the bottom of the scrubber.

In an embodiment the caustic scrubber has several stages with various caustic concentrations. The solvent injection and removal can be located at each stage.

DETAILED DESCRIPTION OF THE INVENTION

Figure 1:
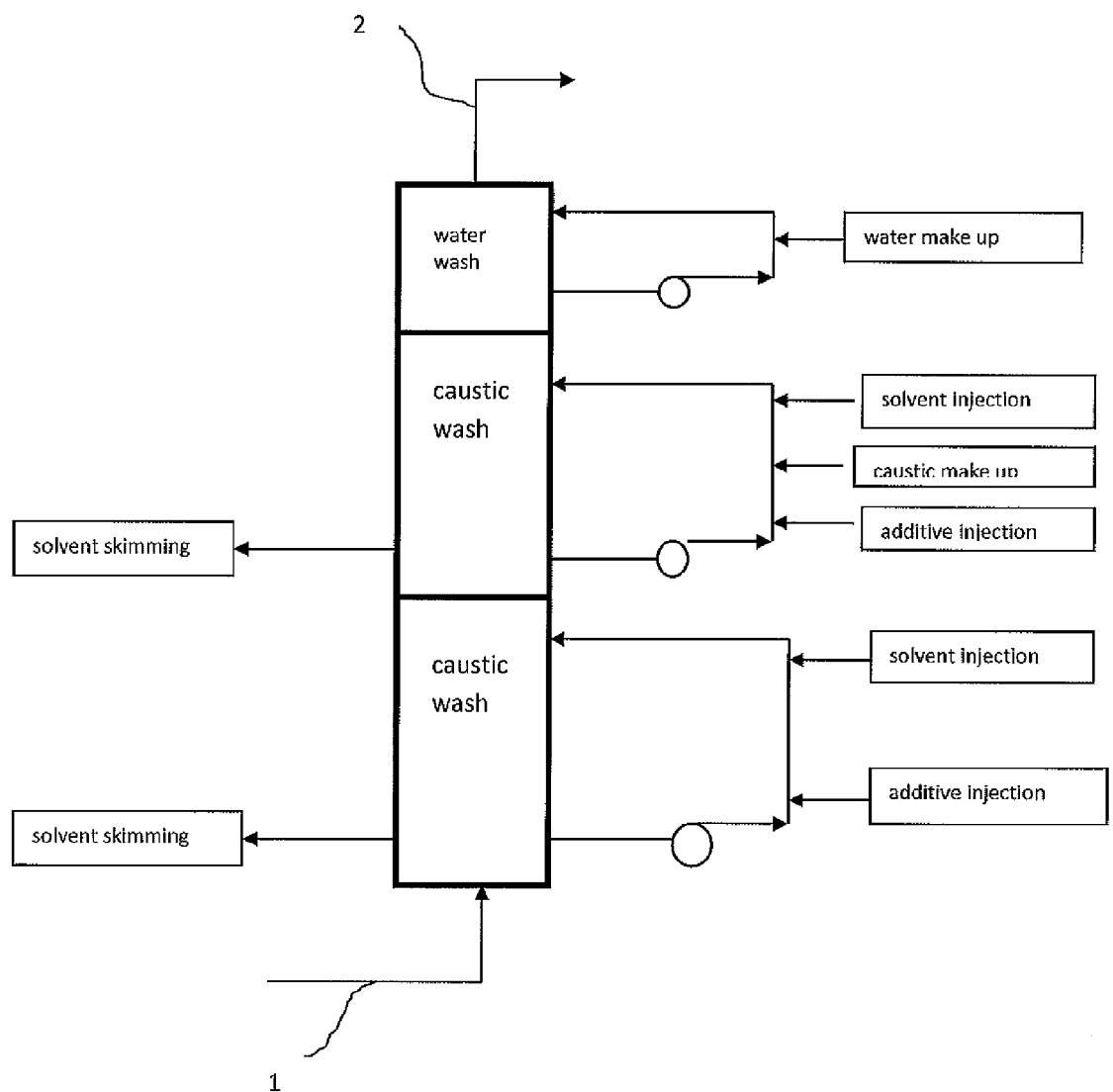
FIG. 1 depicts an embodiment in which an olefin-containing hydrocarbon stream contaminated with oxygenated compounds and acid gases is processed to form an olefin-containing hydrocarbon stream essentially free of acid gases.

As regards the alkaline solution, the concentration of NaOH, KOH or LiOH may range from 3 to 30 w % and advantageously from 5 to 15%. It is advantageously made of NaOH. A caustic make up can be made in one or more parts of the caustic scrubber. A purge of the alkaline solution can be made in one or more parts of the caustic scrubber.

As regards the caustic scrubber, one can cite columns used in conventional absorption systems. In one embodiment, the absorption system uses packed columns, although plate absorption columns may also be used. In another embodiment, the absorption column has a liquid inlet (the alkaline solution) located at a top portion of the absorption column. The absorbent liquid (the alkaline solution) is evenly distributed across the top of the column. Desirably, an even distribution of the absorbent liquid is accomplished by using a distributor plate or spray nozzles. At the bottom of the absorption column is a gas inlet where the olefin-containing hydrocarbon stream, contaminated with oxygenated compounds and acid gases, enters the absorption column. The vapor components move up the column countercurrent to the liquid absorbent moving down the column. This is known as countercurrent absorption. The packing or plates in the column provides a surface for intimate contact between the vapor and liquid components within the column. In a countercurrent absorption column, the concentration of soluble gasses in both the liquid and vapor phases is greatest at the bottom of the column, and lowest at the top of the column. The outlet for the liquid is at the bottom of the absorption column, typically below the gas inlet. The outlet for the gas phase lean in the gasses most soluble in the liquid absorbent is at the top of the absorption column, typically above the liquid inlet. The caustic scrubber can operate at any pressure, advantageously it operates slightly under the pressure of the olefin-containing hydrocarbon stream. The temperature is such as the alkaline solution remains in the liquid state.

In an embodiment the olefin-containing hydrocarbon stream leaving the caustic scrubber is fed to a scrubber fed with water (water scrubber) to remove any alkaline content of said olefin-containing hydrocarbon stream. In a preferred embodiment the water scrubber is on top of the caustic scrubber. In an embodiment in this water scrubber a solvent (hydrocarbon etc . . . ) is injected to wash the water of the Red Oils that are eventually entrained to this top section.

As regards the olefin-containing hydrocarbon stream, contaminated with oxygenated compounds and acid gases, the oxygenated compounds are by way of example carbonyl compounds. All the molecules having a carbon oxygen double bond and that are enolizable can produce Red Oils. These carbonyl compounds include, but are not limited to, aldehydes and ketones. Among the aldehydes one can cite acetaldehyde and propionaldehyde. Among the ketones one can cite acetone, and higher molecular weight ketone. The proportion of oxygenated compounds in the olefin-containing hydrocarbon stream can be up to 1.5 w % and usually ranges from 10 ppm up to 15000 wppm, from 200 to 5000 wppm, more often from 300 to 3000 wppm.

The proportion of acid gases in the olefin-containing hydrocarbon stream may be up to 1 w % and usually ranges from 1 wppm to 1000 wppm. The acid gases can be $CO_2$ and $H_2S$.

The olefin-containing hydrocarbon stream, contaminated with oxygenated compounds and acid gases is coming by way of example from an alcohol dehydration unit or an MTO unit.

As regards the solvent capable to reduce the formation of fouling deposits, it is recommended to select a solvent essentially immiscible with the alkaline solution. The solvent can be an hydrocarbon. One can cite aromatics such as benzene, toluene and xylenes. The solvent can be introduced in the caustic scrubber or in the alkaline solution fed to the scrubber or partly introduced in the caustic scrubber and partly in the alkaline solution fed to the scrubber. The weight ratio of the solvent to the flow of alkaline solution can be up to 0.1 and usually in the range 0.02 to 0.1. The solvent can be introduced in each stage of the caustic scrubber if any. The flow of alkaline solution means the make up of alkaline solution which is the fresh alkaline solution introduced as a compensation of the purge.

As regards the optional additive capable to reduce the conversion of the oxygenated compounds to polymeric fouling deposits in the presence of the alkaline solution, one can cite the oxygenated compounds scavengers and advantageously the carbonyl scavengers. One can cite borohydrides, hydroxylamine and hydroxylamine sulfate.

One can cite U.S. Pat. No. 5,770,041 in which an effective deposit-inhibiting amount of a non-enolizable carbonyl compound is added to the caustic solution. Preferred non-enolizable carbonyl compounds are formaldehyde, glyoxal, benzaldehyde, p-anisaldehyde, formic acid, glyoxalic acid and paraformaldehyde. The non-enolizable carbonyl compound may be added to the spent caustic wash/stripper system in an amount representing a molar ratio of non-enolizable carbonyl to carbonyl from about 25:1 to about 3:1. Preferably, the ratio is from about 10:1 to about 3:1. Most preferably, the ratio is from about 5:1 to about 3:1.

One can cite U.S. Pat. No. 5,194,143 in which an effective amount for the purpose of an acetoacetate ester compound is added to the caustic wash system. Advantageously the ester is of formula $CH_3COCH_2CO_2C_xH_y$ wherein x is an integer from 1 to about 8 and y is an integer from about 3 to about 17. One mole of the acetoacetate ester compound is needed for every one mole of aldehyde. The acetoacetate ester compound should be added to the caustic wash in an amount from about 0.5 to about 10 moles per mole of aldehyde. Preferably, the feed rate ranges to from 1 about 3 moles of acetoacetate ester compound per mole of aldehyde, with a 1.0 mole ratio being especially preferred.

The acetoacetate ester compound should be added to the basic wash in a quantity to assure that the molar amount of acetoacetate ester is sufficient to react with all the undesirable carbonyl contaminants. The present method entails assuring that a sufficient amount of acetoacetate ester compound is present in the basic wash system. The treatment range for the addition of the acetoacetate ester compound to the basic wash system clearly depends upon the severity of the level of impurities in the hydrocarbon to be washed. Broadly speaking, from about 1 to about 10,000 parts per million acetoacetate ester compound per million parts basic wash is a sufficient treatment range if no convenient method of measuring carbonyl level is available.

One can cite U.S. Pat. No. 5,714,055 which comprises adding an effective depositing-inhibiting amount of a caustic solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the caustic solution. A preferred substituted aromatic amine is the sodium salt of 4-amino-benzenesulfonic acid in aqueous solution. The substituted aromatic amine may be added to the alkaline scrubber in an amount representing a molar ratio of amine to carbonyl from about 1.0:10.0 to about 1.0:25.0. Preferably, the substituted aromatic amine may be added to the alkaline scrubber in an amount representing a molar ratio of amine to carbonyl from about 1.0:3.0 to about 1.0:9.0. Most preferably, the substituted aromatic amine may be added to the alkaline scrubber in an amount representing a molar ratio of amine to carbonyl from about 1.0:1.0 to about 1.0:2.0.

One can cite U.S. Pat. No. 6,372,121 wherein a compound selected from the group consisting of alpha-amino acids and esters thereof and amides thereof and salts thereof and mixtures thereof or Mercaptoacetic acid and alkyl esters thereof, is added either to a stream comprising a carbonyl compound or to the basic wash unit operation; wherein the compound is selected such that it remains water-soluble and base-soluble and does not flocculate in the stream or in the basic wash unit operation; and wherein the stream is contacted with the compound either before or at the same time as the stream enters the basic wash unit operation; or wherein the compound is added to the basic wash unit operation before or while the stream enters the basic wash unit operation. The amount of compound added to said stream comprising a carbonyl compound or to the basic wash unit operation is from about 0.01 ppm to about 10,000 ppm, preferably from about 0.1 ppm to about 1000 ppm, and most preferably from about 1 ppm to about 100 ppm.

One can cite U.S. Pat. No. 4,952,301 in which an effective amount for the purpose of an ethylenediamine compound (e.g., ethylenediamine, diethylenetriamine, etc.) is added to the caustic wash system. The treatment should be added to the wash in sufficient quantity to assure that the molar amount of E.D.A. is sufficient to react with all of the undesirable carbonyl contaminants. Treatment ranges of from about 1 to 10,000 ppm of E.D.A. per one million parts of the aqueous scrubbing medium may also be mentioned if no convenient method of measuring carbonyl content is available.

One can cite U.S. Pat. No. 5,220,104 which is directed to the use of a solution of a percarbonate compound of a Group I or Group II metal. A preferred formulation of the percarbonate compound for addition to the basic wash would on a weight basis comprise 10% sodium percarbonate and 90% water. This product would be added to the wash in quantities to assure that the molar ratio of sodium percarbonate to oxygenated or carbonyl compound is 1:1 or greater. Treatment ranges of from about 1 to 10,000 parts of product per million of wash solution could be utilized.

One can cite U.S. Pat. No. 4,673,489 which describes hydroxylamine and its salts. It is theorized that the inhibitors prevent fouling by forming a complex with the carbonyl compounds and that the complex does not undergo polymerization. For one mole of carbonyl compound, one mole of inhibitor is needed. However, since other unknown side reactions could consume the inhibitor, a molar ratio greater than 1:1 should be used. In general, a molar ratio of 1:1 to 10:1 of inhibitor to carbonyl content should suffice, with a preferred ratio of 1:1 to 3:1.

A preferred formulation of the hydroxylamine for addition to the basic wash would on a weight basis comprise 12% hydroxylamine or its chloride or sulfate salts 88% water.

This product would be added to the wash in quantities to assure that the molar ratio of hydroxylamine to oxygenated or carbonyl compound is 1:1 or greater. Treatment ranges of from about 1 to 10,000 parts of product per million of wash solution could be utilized.

One can cite EP264280 relating to a method of inhibiting the formation and deposition of fouling materials in a basic solution in the washing of hydrocarbon streams. The method entails adding to the basic wash a sufficient amount of water-soluble sulfite or bisulfite to inhibit fouling due to polymer formation of oxygenated hydrocarbon components.

One can cite non-enolizable carbonyl compounds, by way of example, aldoses such as glyceraldehydes or higher molecular weight aldose. The aldoses are defined as compounds having a terminal aldehyde and a global composition $(CH_2O)_n$. The derivatives from these aldoses where the non-enolizable aldehyde group remains can also be efficient. The hydrolizable dimmers of aldoses can also be efficient because they will be hydrolyzed in the scrubber.

FIG. 1 describes an embodiment of the invention. 1 is the olefin-containing hydrocarbon stream, contaminated with oxygenated compounds and acid gases, 2 is the olefin-containing hydrocarbon stream essentially free of acid gases. In said embodiment there are 2 caustic scrubbers and a water scrubber on top.

EXAMPLES

In all the examples the alkaline solution is a NaOH solution.

The first experiments are a comparison of various aldehydes or ketones for the Polyaldols formation. We see clearly that the acetaldehyde is the best Polyaldols precursor. This is not a surprise regarding the acidity of hydrogen groups of the methyl part of the molecule.

Figure 2:
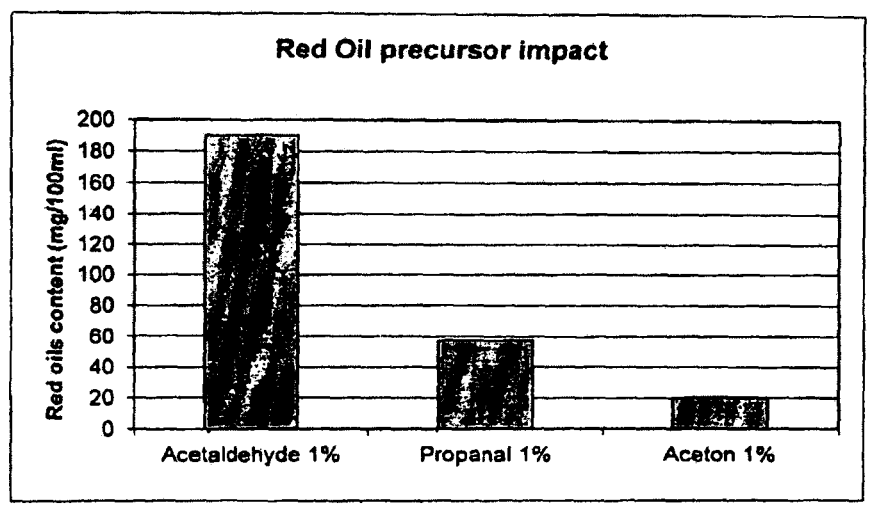
FIG. 2 depicts a bar graph of red oils content with respect to acetaldehyde content, propanol content, and acetone content.

See FIG. 2, in which the conditions are: 40° C., 1% precursor, 30 minutes, and 8% Caustic. If we change the acetaldehyde concentration, the quantity of polyaldols we produce is rather linear with the acetaldehyde concentration. But, if we assume that we produce a polyaldols average with 5 acetaldehydes the maximum Polyaldols content is 660 mg/100 ml for 1000 ppm initial concentration. This is only an average because in reality we have a mixture of different molar weight Polyaldols. Based on this assumption, we see that the Polyaldol yield increases with the acetaldehyde concentration.

Figure 3:
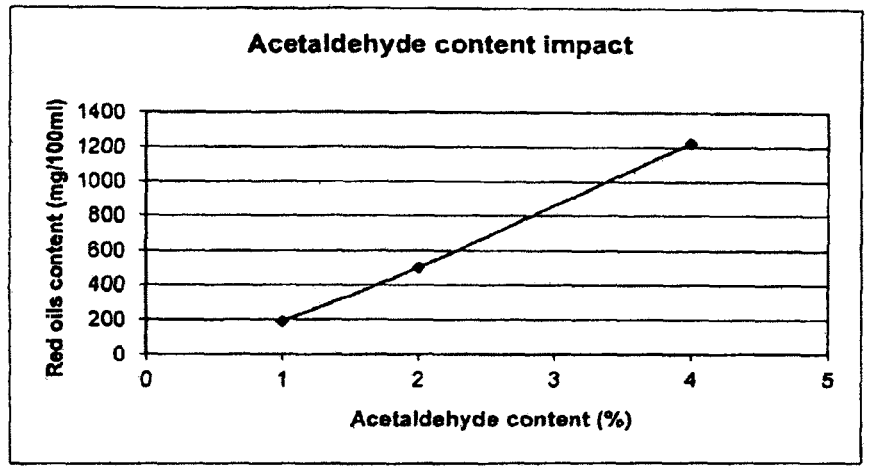
FIG. 3 depicts a plot of red oils content versus acetaldehyde content.

See FIG. 3, in which the conditions are: 40° C., 30 minutes, and 8% Caustic.

Figure 4:
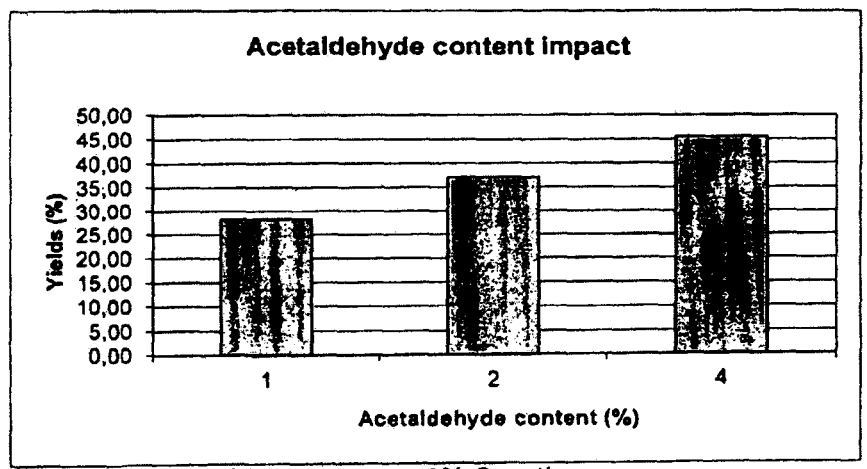
FIG. 4 depicts a bar graph of polyaldol yield with respect to acetaldehyde content.

Also, see FIG. 4, in which the conditions are: 40° C., 30 minutes, and 8% Caustic.

In Caustic Tower the residence time on the active area is around 30 mn, so we made the experiments around this residence time. In our conditions, the Polyaldols formation is more or less linear with time. This shows the interest to decrease the residence time in dead zones and to renew the caustic.

Figure 5:
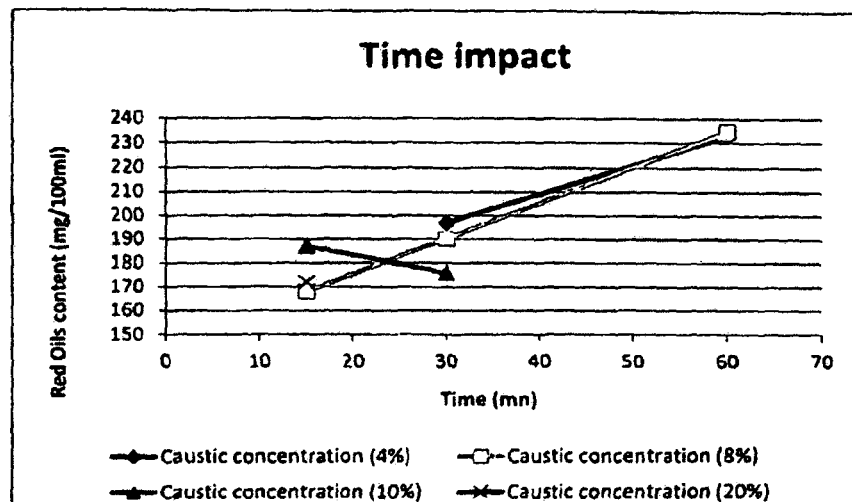
FIG. 5 depicts a plot of red oils content with respect to time at different caustic concentrations.

See FIG. 5, in which the conditions are: 40° C., and 1% acetaldehyde.

Figure 6:
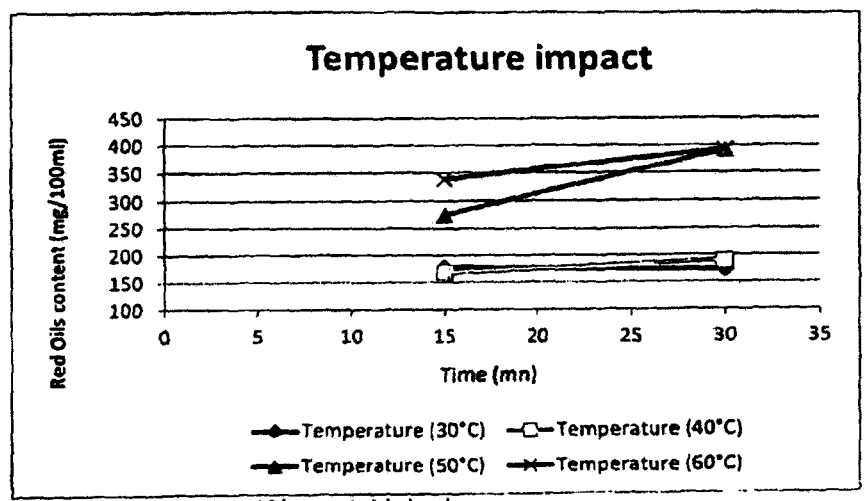
FIG. 6 depicts a plot of red oils content with respect to time at different temperatures.

On the following chart shown in FIG. 6, we see clearly that over 40° C., the temperature has an important impact of the yields.

See FIG. 6, in which the conditions are: 8% caustic, and 1% acetaldehyde. Note: the point at 60° C. and 30 mn in FIG. 6 is lowered because the yield is becoming important (around ⅔ of Acetaldehyde is consumed). This high yield has an impact on Red Oils polymerization kinetic.

Figure 7:
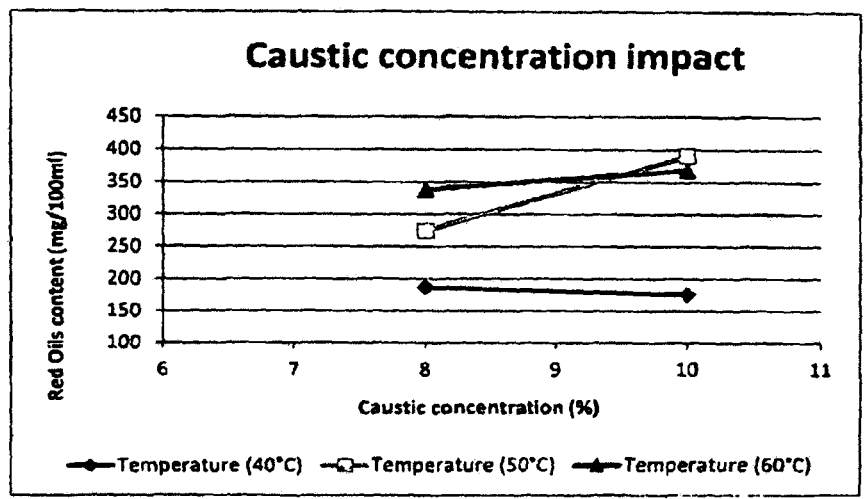
FIG. 7 depicts a plot of red oils content with respect to caustic concentration at different temperatures.

The caustic concentration has also an impact, as shown in FIG. 7.

See FIG. 7, in which the conditions are: 15 minutes, and 1% Acetaldehyde. Note: the point at 60° C. and 10% in FIG. 7 is lowered because the yield is becoming important (around ⅔ of Acetaldehyde is consumed).

On some Steamcracker Caustic Tower we use Wash Oils, or we have some aromatics condensation. We tested the impact of the presence of Toluene on the Polyaldols formation. We see clearly that the presence of a solvent, while extracting the Polyaldols, reduces their formation.

Figure 8:
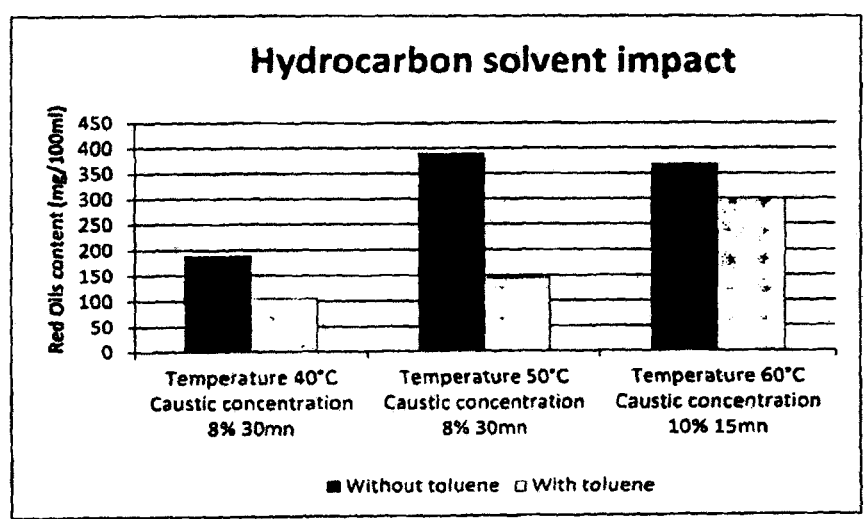
FIG. 8 depicts a bar graph of red oils content at differing temperatures, caustic concentrations, and time, both with and without toluene.

See FIG. 8, in which the conditions are: 1% Acetaldehyde.

We tested two different types of additives. NaBH4 hydrogenates the aldehyde function, and the hydroxylamine produces an oxyme with the aldehyde. We made the first tests with the same potential conversion of acetaldehyde. We see clearly that the hydroxylamine sulfate seems to be the most active. But the difference is in the reaction and the kinetic is probably different. The main difference between our test and the industrial situation is that we mix rapidly all the acetaldehyde in the caustic and we mix the entire additive. In the industrial situation we are in an equilibrated state with a continuous absorption of the acetaldehyde and a continuous addition of additive. The other difference is that with the NaBH4 we add normally the entire stoechiometric quantity of additive.

Figure 9:
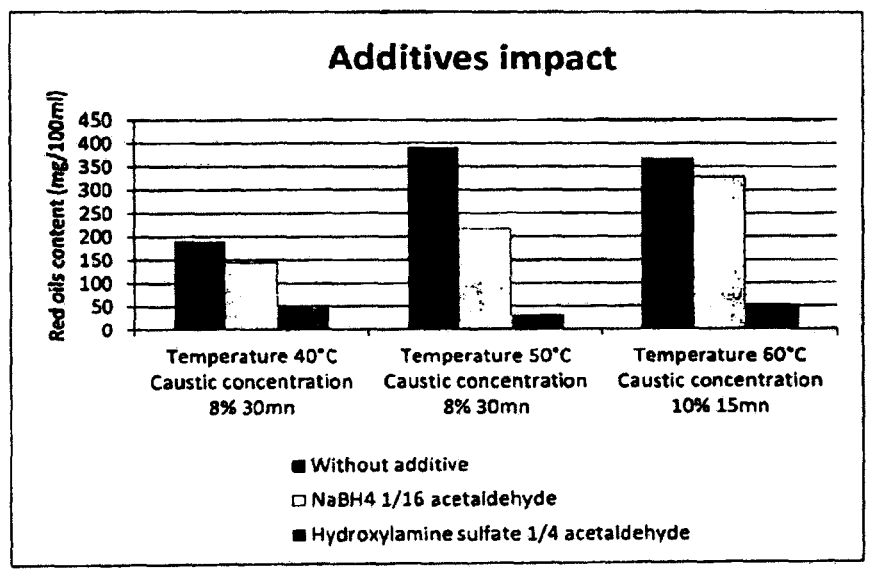
FIG. 9 depicts a bar graph of red oils content at differing temperatures, caustic concentrations, and time with additive, with $NaBH_4$ and acetaldehyde, and with hydroxylamine sulfate and acetaldehyde.

See FIG. 9, in which the conditions are: 1% Acetaldehyde.

What is claimed:

1. A method of reducing the formation of fouling deposits occurring in a caustic scrubber used to remove acid gases comprising:
   a) providing a caustic scrubber fed with an alkaline aqueous solution comprising essentially one or more of NaOH, KOH or LiOH,
   b) providing an olefin-containing hydrocarbon stream, contaminated with oxygenated compounds and acid gases, and said oxygenated compounds are capable to make polymeric fouling deposits in the presence of the alkaline aqueous solution of the caustic scrubber,
   c) sending the above olefin-containing hydrocarbon stream to the caustic scrubber to recover an olefin-containing hydrocarbon stream essentially free of acid gases,
   wherein,
   d) an efficient amount of a solvent capable to reduce the formation of fouling deposits is introduced in the caustic scrubber and/or in the alkaline aqueous solution fed to the caustic scrubber,
   e) a liquid outlet of the caustic scrubber is sent to means to separate the solvent from the alkaline aqueous solution,
   f) optionally an additive capable to reduce the conversion of the oxygenated compounds to polymeric fouling deposits in the presence of the alkaline aqueous solution of the caustic scrubber is introduced in the caustic scrubber and/or in the alkaline aqueous solution fed to the caustic scrubber;
   wherein the caustic scrubber has several stages with various caustic concentrations, and wherein solvent injection and removal are located at each stage.

2. The method according to claim 1 wherein the solvent separated from the alkaline aqueous solution at step e) is treated to eliminate heavies and recycled at step d).

3. The method according to claim 1 wherein the means of step e) to separate the solvent from the alkaline aqueous solution are located in a bottom of the caustic scrubber.

4. The method according to claim 1 wherein the oxygenated compounds are carbonyl enolizable components.

5. The method according to claim 1 wherein the proportion of oxygenated compounds in the olefin-containing hydrocarbon stream is up to 15000 wppm.

6. The method according to claim 5 wherein the proportion of oxygenated compounds in the olefin-containing hydrocarbon stream ranges from 10 ppm up to 15000 wppm.

7. The method according to claim 1 wherein the proportion of acid gases in the olefin-containing hydrocarbon stream is up to 1%.

8. The method according to claim 7 wherein the proportion of acid gases in the olefin-containing hydrocarbon stream ranges from 1 ppm to 1000 ppm.

9. The method according to claim 1 wherein the weight ratio of the solvent to the flow of alkaline aqueous solution is up to 0.1.

10. The method according to claim 1 wherein the olefin-containing hydrocarbon stream leaving the caustic scrubber is fed to a scrubber fed with water to remove any alkaline content of said olefin-containing hydrocarbon stream.

11. The method according to claim 10 wherein the scrubber fed with water is on top of the caustic scrubber.

12. The method according to claim 10 wherein a solvent is injected in the scrubber fed with water to wash the water of the Red Oils that are eventually entrained to this top section.

13. The method according to claim 1 wherein the weight ratio of the solvent to the flow of alkaline aqueous solution is in the range 0.02 to 0.1.

* * * * *